United States Patent
Orr

(10) Patent No.: US 12,067,324 B2
(45) Date of Patent: Aug. 20, 2024

(54) VIRTUAL AND AUGMENTED REALITY TELECOMMUNICATION PLATFORMS

(71) Applicant: XR Health IL LTD, Tel Aviv (IL)

(72) Inventor: Eran Orr, Brookline, MA (US)

(73) Assignee: XR Health IL LTD, Tel Aviv (IL)

( * ) Notice: Subject to any disclaimer, the term of this patent is extended or adjusted under 35 U.S.C. 154(b) by 953 days.

(21) Appl. No.: 16/991,425

(22) Filed: Aug. 12, 2020

(65) Prior Publication Data
US 2020/0371738 A1    Nov. 26, 2020

Related U.S. Application Data

(63) Continuation of application No. PCT/US2019/017514, filed on Feb. 11, 2019.
(Continued)

(51) Int. Cl.
*G06F 3/14*    (2006.01)
*A61B 5/00*    (2006.01)
(Continued)

(52) U.S. Cl.
CPC .......... *G06F 3/1454* (2013.01); *A61B 5/0022* (2013.01); *A61B 5/4833* (2013.01);
(Continued)

(58) Field of Classification Search
CPC ........ G06F 3/1454; G06F 3/011; G06F 3/017; G06F 3/0346; A61B 5/0022;
(Continued)

(56) References Cited

U.S. PATENT DOCUMENTS

| | | | | |
|---|---|---|---|---|
| 5,429,140 A | * | 7/1995 | Burdea | A63B 21/008 600/587 |
| 6,425,764 B1 | * | 7/2002 | Lamson | G16H 30/40 434/236 |

(Continued)

FOREIGN PATENT DOCUMENTS

| | | | | |
|---|---|---|---|---|
| JP | 2014502178 A | * | 1/2014 | |
| JP | 2014502178 A | * | 7/2014 | |

(Continued)

OTHER PUBLICATIONS

International Search Report and Written Opinion for International Application No. PCT/US2019/017514 dated Feb. 11, 2019.

*Primary Examiner* — Jeffrey S Vanderveen
(74) *Attorney, Agent, or Firm* — Foley Hoag LLP; Erik A. Huestis; Joshua S. Matloff

(57) ABSTRACT

Provided herein are clinical evaluation and treatment as well as training protocols in virtual or augmented reality that create fully immersive environments, which enable real-time rendering for communication, specifically telecommunication, between two or more parties. In various embodiments, a virtual environment is provided to a first user at a first location. A first set of data comprising positional data of the first user is provided to a second user (e.g., an instructor) at a second location. An activity (e.g., a treatment or assessment protocol) may be received from the second user (e.g., an instructor) and the activity may be displayed to the first user via layering the activity over the virtual environment. An adjustment may be applied to the activity by the second user based on compliance of the first user with the activity protocols. Additional users at other locations may also receive the first activity from the second user.

11 Claims, 9 Drawing Sheets

Related U.S. Application Data

(60) Provisional application No. 62/629,441, filed on Feb. 12, 2018.

(51) Int. Cl.
| | | |
|---|---|---|
| *A61B 90/00* | (2016.01) | |
| *G06F 3/01* | (2006.01) | |
| *G06T 11/00* | (2006.01) | |
| *G16H 15/00* | (2018.01) | |
| *G16H 20/30* | (2018.01) | |
| *G16H 40/67* | (2018.01) | |
| *G16H 70/20* | (2018.01) | |
| *G16H 80/00* | (2018.01) | |

(52) U.S. Cl.
CPC .............. *G06F 3/011* (2013.01); *G06T 11/00* (2013.01); *G16H 40/67* (2018.01); *G16H 80/00* (2018.01); *A61B 2090/365* (2016.02); *A61B 2505/09* (2013.01); *G16H 15/00* (2018.01); *G16H 20/30* (2018.01); *G16H 70/20* (2018.01)

(58) Field of Classification Search
CPC ............ A61B 5/4833; A61B 2090/365; A61B 2505/09; A61B 5/1123; A61B 5/0205; A61B 5/02055; A61B 5/117; A61B 5/225; A61B 2562/0219; A61B 5/1114; A61B 5/1118; A61B 5/70; G06T 11/00; G16H 40/67; G16H 80/00; G16H 15/00; G16H 20/30; G16H 70/20; G02B 27/017
See application file for complete search history.

(56) References Cited

U.S. PATENT DOCUMENTS

| | | | |
|---|---|---|---|
| 2012/0143358 A1* | 6/2012 | Adams ................ | G06F 3/04815 700/92 |
| 2015/0306340 A1* | 10/2015 | Giap ........................ | A61B 6/46 600/301 |
| 2015/0348330 A1* | 12/2015 | Balachandreswaran ..................... | A63F 13/212 463/32 |
| 2019/0030394 A1* | 1/2019 | Orr ........................ | G16H 20/30 |
| 2019/0224528 A1* | 7/2019 | Omid-Zohoor ...... | A61B 5/6806 |
| 2020/0126284 A1* | 4/2020 | Garofalo ................ | G16H 40/67 |
| 2021/0409449 A1* | 12/2021 | Crabtree ............. | H04L 63/1441 |
| 2022/0406473 A1* | 12/2022 | Arbel ................... | G06F 3/1454 |

FOREIGN PATENT DOCUMENTS

| | | | | |
|---|---|---|---|---|
| WO | WO-2017/115366 | | 7/2017 | |
| WO | WO-2017115366 A1 | * | 7/2017 | ......... A63B 21/0442 |

* cited by examiner

VIRTUAL AND AUGMENTED REALITY TELECOMMUNICATION PLATFORMS

CROSS-REFERENCE TO RELATED APPLICATIONS

This application is a continuation of International Application No. PCT/US2019/017514, filed Feb. 11, 2019, which claims the benefit of U.S. Provisional Application No. 62/629,441 filed Feb. 12, 2018, each of which is hereby incorporated by reference in its entirety.

BACKGROUND

Embodiments of the present disclosure relate to virtual and augmented reality telecommunication platforms, and more specifically, to multi-layered real-time virtual and augmented reality telecommunication platforms for treatment, training, and patient evaluation.

BRIEF SUMMARY

According to embodiments of the present disclosure, systems for, methods of, and computer program products for clinical evaluation and treatment in virtual or augmented reality are provided. In various embodiments, a virtual environment is provided to a first user via a virtual or augmented reality system at a first location. A first set of data is collected based on the first user's interaction with the virtual environment. The first set of data includes positional data of the first user. The first set of data is provided a second user at a second location via a network. A first activity is received from the second user. The first activity is displayed to the first user by layering the first activity over the virtual environment. A second set of data related to the first user and the first activity in the virtual environment is collected. The second set of data includes positional data of the first user. A compliance metric may be determined based on the second set of data. When the compliance metric differs from a predetermined range, an adjustment is applied to the first activity. The adjustment is based on the second set of data. The adjusted first activity is displayed to the first user by layering the adjusted first activity over the virtual environment.

In some embodiments, the virtual environment is provided to a second user via the virtual or augmented reality system, wherein the second user is enabled to interact with the first user.

In various embodiments, a system is provided including a virtual or augmented reality system, comprising a virtual or augmented reality display adapted to display a virtual environment to a first user, one or more biometric sensors coupled to the first user, and a computing node comprising a computer readable storage medium having program instructions embodied therewith. The program instructions are executable by a processor of the computing node to cause the processor to perform a method where a virtual environment is provided to a first user via a virtual or augmented reality system at a first location. A first set of data is collected based on the first user's interaction with the virtual environment. The first set of data includes positional data of the first user. The first set of data is provided a second user at a second location via a network. A first activity is received from the second user. The first activity is displayed to the first user by layering the first activity over the virtual environment. A second set of data related to the first user and the first activity in the virtual environment is collected. The second set of data includes positional data of the first user. A compliance metric may be determined based on the second set of data. When the compliance metric differs from a predetermined range, an adjustment is applied to the first activity. The adjustment is based on the second set of data. The adjusted first activity is displayed to the first user by layering the adjusted first activity over the virtual environment.

In various embodiments, a computer program product for providing a virtual or augmented reality platform. The computer program product includes a computer readable storage medium having program instructions embodied therewith to perform a method where a virtual environment is provided to a first user via a virtual or augmented reality system at a first location. A first set of data is collected based on the first user's interaction with the virtual environment. The first set of data includes positional data of the first user. The first set of data is provided a second user at a second location via a network. A first activity is received from the second user. The first activity is displayed to the first user by layering the first activity over the virtual environment. A second set of data related to the first user and the first activity in the virtual environment is collected. The second set of data includes positional data of the first user. A compliance metric may be determined based on the second set of data. When the compliance metric differs from a predetermined range, an adjustment is applied to the first activity. The adjustment is based on the second set of data. The adjusted first activity is displayed to the first user by layering the adjusted first activity over the virtual environment.

DETAILED DESCRIPTION

Figure 1:
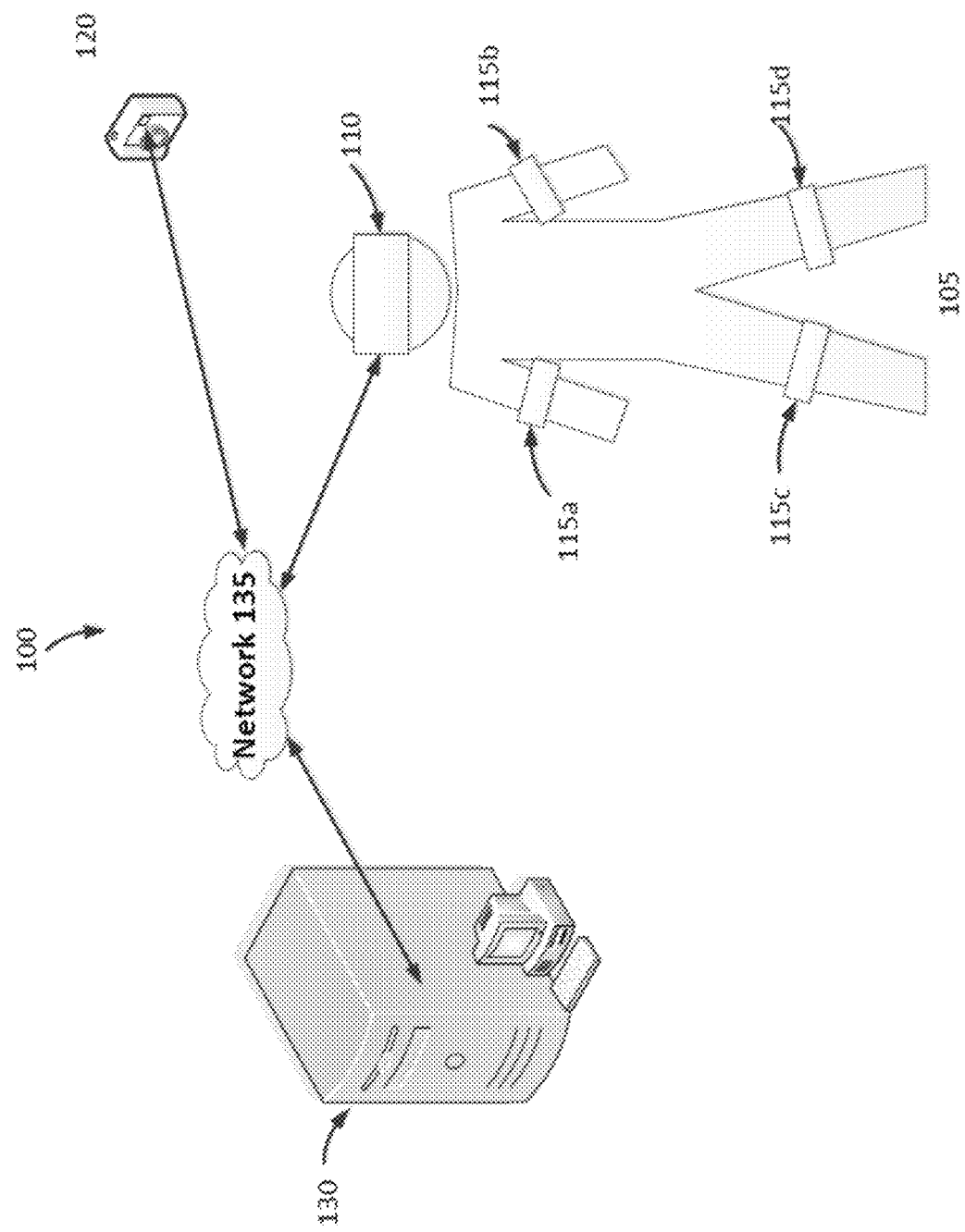
FIG. 1 is a simplified illustration of a multi-layer real-time Virtual Reality telecommunications systems (VRTS), in accordance with an embodiment of the present disclosure.

Currently, real-time telecommunication software is based on a single audio/video feed, and has no ability to add multiple layers of visual and auditory content. Similarly, existing systems do not allow manual real-time manipulation of the telecommunication environment. Existing solutions do not accommodate the need to customize the output to the specific needs of a user. Thus, there remains a need in the art for real-time telecommunication software that comprises multi-layered visual and auditory content, and which can be manipulated manually or automatically, so as to customize the output to the specific needs of one or more users.

In various embodiments, the current disclosure provides a multi-layer real-time Virtual Reality telecommunication system (VRTS). In various embodiments, the VRTS provides an immersive virtual environment to one or more users. In some embodiments, the VRTS enables one or more user to treat one or more other user using the VRTS. In some embodiments, the VRTS enables real-time data collection and/or treatment of one or more users interacting with a virtual environment provided by the VRTS.

In various embodiments, the VRTS includes a data storage system, one or more cameras, and a communication system. The user(s) of the VRTS may use one or more sensors that can provide the VRTS information about the interaction of one or more user with the virtual environment provided by the VRTS. In some embodiments, the user(s) of the VRTS use a headset (for example, the headset described below with reference to FIG. 7) in communication with the VRTS to provide an immersive virtual environment to each user. In further embodiments, the user(s) can use interactive gloves, tools, and/or other controls with that allow for interaction with the virtual environment. In various embodiments, the user(s) may attach a mobile device to their body to collect data via, e.g., an internal gyroscopes and/or accelerometer.

In various embodiments, a first user can interact, in real-time, with one or more additional users (e.g., a second user, a third user, a fourth user, etc.) connected to the VRTS. In some embodiments, one or more users can access collected data related to the first user. In some embodiments, one or more users can use collected data to provide one or more treatments, tasks, and/or information to the first user utilizing the VRTS. In some embodiments, a VRTS may be enabled to recommend one or more treatments based on the collected data.

In various embodiments, the VRTS may provide treatments, tasks, or information, on a per user basis by layering the treatment, task, and/or information, over the virtual environment. For example, in one embodiment, a specific exercise may be shown and/or provided to one user while a different exercise may be shown to a second user. The VRTS may adjust each exercise as needed for each user to tailor the exercises to the specific user by collecting positional data over time for each user as they perform the exercises. In various embodiments, the adjustments may be manually implemented by another user, e.g., an instructor or therapist. In various embodiments, the adjustment may be automatically implemented by the VRTS based on a predetermined threshold of compliance with the exercise requirements.

It will be appreciated that a variety of virtual and augmented reality devices are known in the art. For example, various head-mounted displays providing either immersive video or video overlays are provided by various vendors. Some such devices integrate a smart phone within a headset, the smart phone providing computing and wireless communication resources for each virtual or augmented reality application. Some such devices connect via wired or wireless connection to an external computing node such as a personal computer. Yet other devices may include an integrated computing node, providing some or all of the computing and connectivity required for a given application.

Virtual or augmented reality displays may be coupled with a variety of motion sensors in order to track a user's motion within a virtual environment. Such motion tracking may be used to navigate within a virtual environment, to manipulate a user's avatar in the virtual environment, or to interact with other objects in the virtual environment. In some devices that integrate a smartphone, head tracking may be provided by sensors integrated in the smartphone, such as an orientation sensor, gyroscope, accelerometer, or geomagnetic field sensor. Sensors may be integrated in a headset, or may be held by a user, or attached to various body parts to provide detailed information on user positioning.

In various embodiments, additional sensors are included to measure characteristics of a subject in addition to motion. For example, cameras and microphones may be included to track speech and facial features. Biometric sensors may be included to measure features such as heart rate, blood pressure, glucose, temperature, or galvanic skin response.

In various embodiments, a user is furnished with a VR or AR system. As noted above, a VR or AR system will generally have integrated motion sensors. In addition, additional motions sensors may be provided, for example to be handheld. This allows tracking of multiple patient attributes while they interact with a scene. In this way, systematic and reproducible scenarios may be used to assess the subject's function.

In various embodiments, patient motion may be tracked. For example, Gait, Stability, Tremor, Amplitude of Motion, Speed of Motion, and Range of Motion may be measured. Movement may be analyzed to determine additional second order attributes such as smoothness or rigidity.

The tracking of these metrics allows the generation of quantified, detailed reports that are aligned with common practice evaluation procedures. It will be appreciated that a variety of evaluation protocol are known in the art.

FIG. 1 is a simplified illustration of a multi-layer real-time Virtual Reality telecommunications systems (VRTS), in accordance with embodiments of the present disclosure. As shown in FIG. 1, the VRTS 100 includes a data storage system 130, a network 135, a camera 120, sensors (115*a*-115*d*, 115, generally), and a Virtual Reality (VR) headset 110. The user 105 is wearing sensors 115 can provide information about the user 105 to the data storage system 130. In addition, camera 120 can provide motion data of the user. In many embodiments, the VRTS may use one or more data storage systems, one or more sensors, and one or more cameras to monitor, record, and/or track data related to the user. In this embodiment, each portion of the VRTS 100 is in communication with other portions of the VRTS 100 through a wireless connection. In some embodiments, one or more portions may be connected using wired connections.

Figure 2:
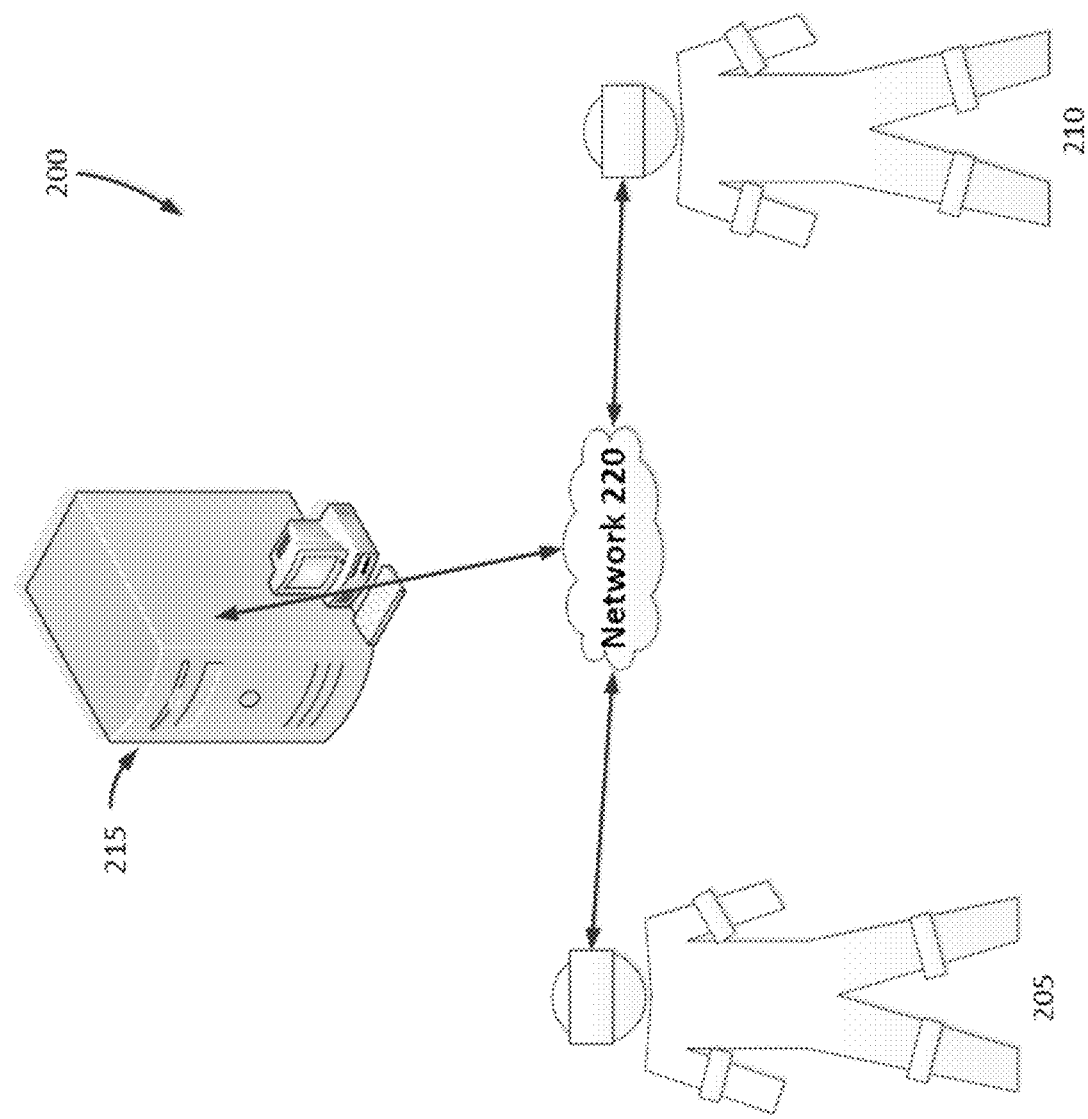
FIG. 2 is a simplified illustration of a multi-layer real-time Virtual Reality Telecommunications system (VRTS), in accordance with an embodiment of the present disclosure.

FIG. 2 is a simplified illustration of a multi-layer real-time Virtual Reality Telecommunications system (VRTS), in accordance with embodiments of the present disclosure. In some such embodiments, the VRTS 200 includes data storage system 215, network 220, user 205 and user 210. User 205 and user 210 are interacting with each other within a virtual environment provided by data storage system 215. Each portion of the VRTS 200 are in communication with each other portion of the VRTS 200 using network 220. In this embodiment, network 220 represents a wireless network through which data from user 205 and user 210 is collected and/or stored by data storage system 215. As shown, user 210 is enabled to access data stored on the data storage system 215, and can affect the virtual environment by adding one or more layers onto the virtual environment.

Figure 3:
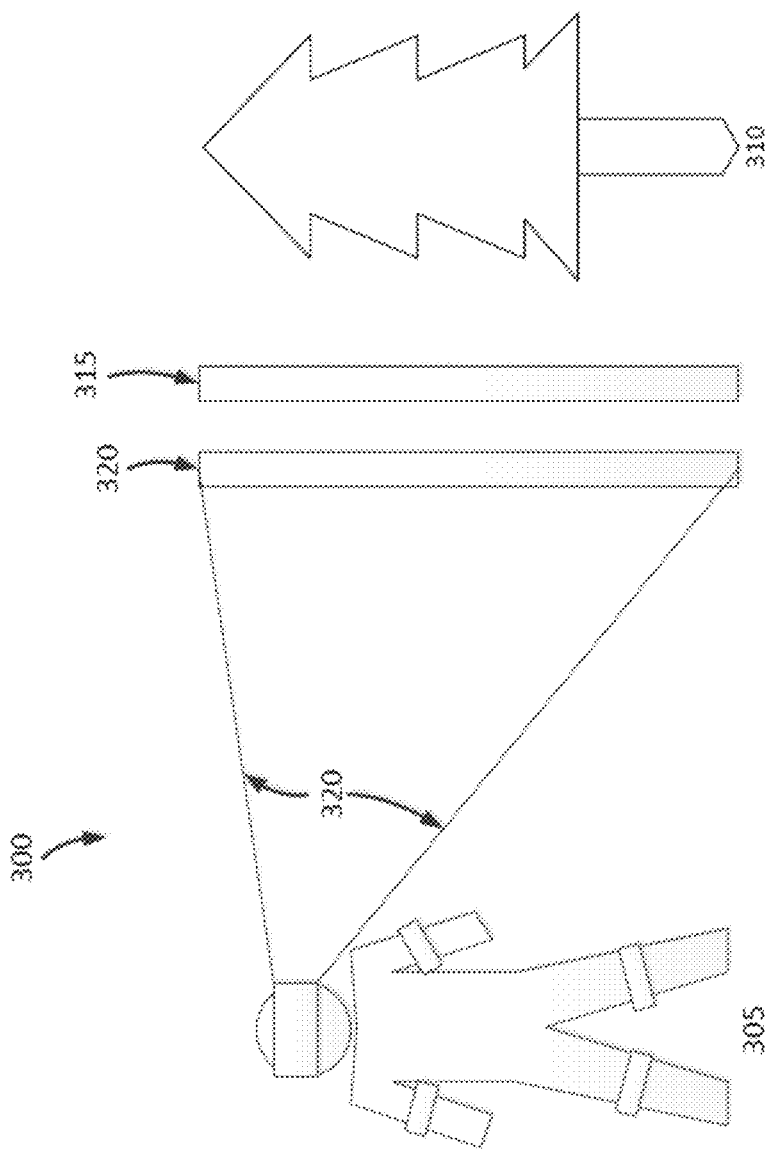
FIG. 3 is a simplified illustration of a view of a user using a multi-layer real-time Virtual Reality Telecommunication system (VRTS), in accordance with an embodiment of the present disclosure.

FIG. 3 is a simplified illustration of a view of a user using a multi-layer real-time Virtual Reality Telecommunication system (VRTS), in accordance with embodiments of the present disclosure. User 305 is using the VRTS 300 to interact with a virtual environment 310. The user's 305 field of view is shown by arrows 320. In this embodiment, one or more layers may be implemented over the virtual environment 310 to affect the user's 305 view of the virtual environment 310. In this instance, the VRTS 300 has placed layer 320 and layer 315 overlayed on top of the virtual environment 310. In some embodiments, a layer overlayed on a virtual environment may be a treatment, task, and/or additional information enabled to be seen by one or more users.

Figure 4:
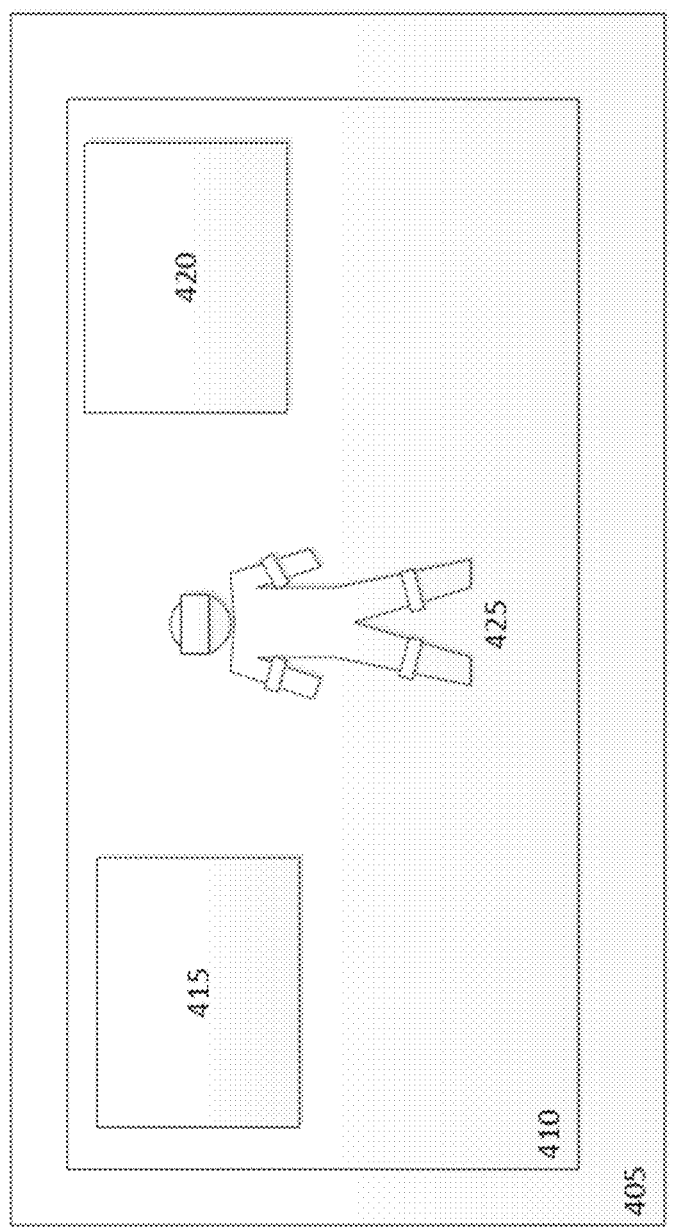
FIG. 4 is a simplified illustration of a user's view through a virtual reality headset in a multi-layer real-time Virtual Reality telecommunications system (VRTS), in accordance with an embodiment of the present disclosure.

FIG. 4 is a simplified illustration of a user's view through a virtual reality headset in a multi-layer real-time Virtual Reality telecommunications system (VRTS), in accordance with embodiments of the present disclosure. Virtual reality headset 405 includes screen 410. In this instance, the screen 410 is showing user 425 within a virtual environment. Information 415 and 420 is overlayed on top of the virtual environment. In some embodiments, the overlayed information may be information related to one or more users using the VRTS. In various embodiments, the overlayed information may be treatments or tasks to be completed by one or more users utilizing the VRTS.

In various embodiments, a method of treating a user using a multi-layer real-time Virtual Reality Telecommunication System (VRTS) as shown in FIG. 2 is provided, in accordance with embodiments of the present disclosure. The VRTS 200 includes a data storage system 215, a network, and user 205 and user 210. VRTS 200 provides a virtual environment to users 205, 210 using the data storage system 215. Data Storage System 215 collects data from both user 205 and user 210 using sensors attached to users 205 and user 210. Data Storage system 215 is enabled to analyze the collected data to determine a first treatment. In some embodiments, the user(s) may be enabled to analyze data and prescribe one or more treatments to another user based on the data. Data storage system 215 implements the first treatment by layering the first treatment over the virtual environment provided by the data storage system 215. The data storage system 215 collects data related to user 205 and the first treatment. The data storage system 215 analyzes the collected data and applies one or more adjustments to the first treatment.

The systems and methods provided herein allow creation of a fully immersive environment that includes one or more participants. For example, a omnidirectional camera may be placed in a location such as a gym or treatment center. Each participant may view a live video representation of that location from one or more location. The participants may see a 3-dimensional figure of the other participants, allowing a greater ability to connect and evaluate. For example, a plurality of exercise participants may be connected to a single video stream of a gym or treatment center with an instructor present. As described above, audio and video making up a complete virtual environment including the instructor may be provided to each participant. The instructor may be provided real-time data regarding each participant, for example through a handheld device. In turn, the instructor may control in real time the overlays on the virtual environment for each participant.

The VR overlays allows manipulation of a live environment, for example by adding multiple layers to the environment to create different tasks and situations for participants. This allows for more precise evaluation, training, and treatment while monitoring the user constantly and providing immediate feedback for different providers. This integrated VR platform reduces costs and improves objectivity and accessibility to accurate measurements and detailed outputs.

It will be appreciated that the present disclosure is useful to a variety of users in a variety of contexts. For example, a first user may be a healthcare provider, coach, or trainer, while a second user may be a patient, athlete, or trainee. Based on real-time analysis of user performance, quantified reports may be provided according to common practice evaluation procedures. The first user may then customize the training or treatment regimen and provide one or more additional layers of output in the virtual environment for the second user. In this way, a customized virtual training or treatment session is provided. Ongoing monitoring and analysis may be provided, and the data may be provided to both users. Continuous, real-time communication is provided among the users.

Figure 5A:
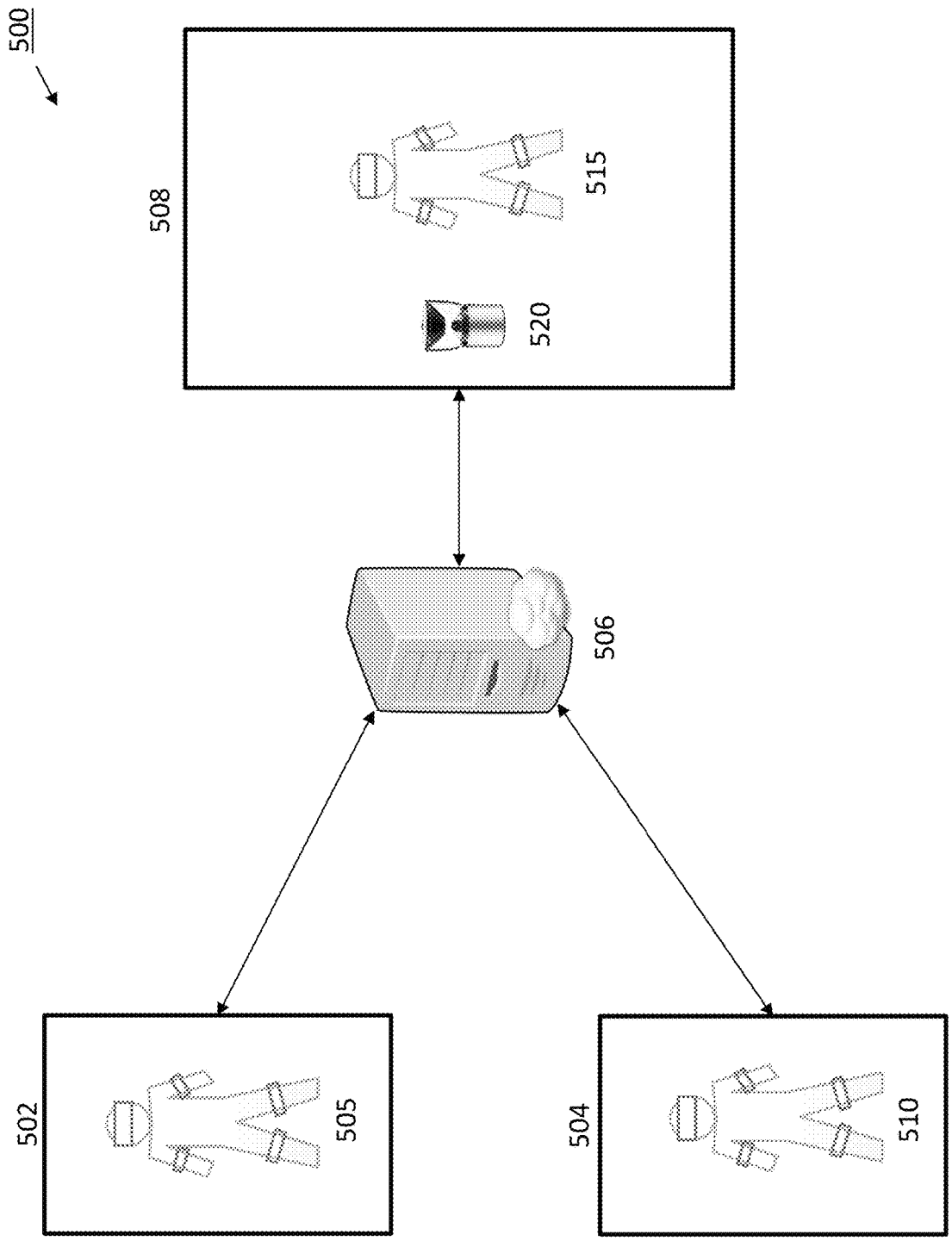
FIG. 5A is a simplified illustration of a multi-layer real-time Virtual Reality Telecommunications system (VRTS), in accordance with an embodiment of the present disclosure.

FIG. 5A illustrates a multi-layer real-time Virtual Reality Telecommunications system (VRTS) 500, in accordance with an embodiment of the present disclosure. The VRTS 500 includes a first user 505 at a first location 502 and a second user 510 at a second location 504. In various embodiments, the first location 502 and the second location 504 may be different locations (e.g., each user's residence). In various embodiments, the first location 502 and the second location 504 may be the same locations (e.g., a common space accessible to multiple users). The first user 505 and the second user 510 may be wearing the VR/AR headset and/or motion tracking sensors as described in more detail with respect to FIG. 7.

In various embodiments, the VRTS 500 includes a third user 515 at a third location 508. In various embodiments, the third user may be wearing the VR/AR headset and/or motion tracking sensors as described in more detail with respect to FIG. 7. In various embodiments, the third user 515 may be an instructor, trainer, physical therapist, or other healthcare provider. In various embodiments, the third user 515 may transmit video to the first user 505 and the second user 510 via a camera 520 connected to a computer node implementing the VRTS 500. In various embodiments, the camera 520 may be a digital camera. In various embodiments, the camera 520 may be an omnidirectional camera. The video feed recorded by the camera 520 may be displayed to the first user 505 and the second user 510 within the virtual environment so that the first user 505 and the second user 510 may view the third user 515 in real time. In various embodiments, the first user 505, the second user 510, and/or the third user 515 may be represented within VRTS 500 as digital avatars or other digital representations as are known in the art. In various embodiments, the users 505, 510, and/or 515 may interact with one another in the VRTS 500. For example, the third user 515 may demonstrate an activity, such as a treatment protocol or an assessment protocol, to one or more users 505, 510 connected to the system.

In various embodiments, the VRTS 500 may record treatment protocol, rehabilitation protocol, and/or assessment protocol sessions with the third user 515 such that the first user 505 and/or the second user 510 may access the recorded sessions in the future or at least until sessions are no longer required (e.g., when rehabilitation has been determined to be completed).

In various embodiments, computer nodes implementing the VRTS 500 for the first user 505, the second user 510, and the third user 515 are connected via a network to one or more remote servers 506. In various embodiments, the remote server 506 may be a cloud server. In various embodiments, the remote server 506 may be located at the location of, e.g., the instructor or company providing the treatment or assessment protocols. In various embodiments, the one or more servers 506 may include a database, such as, for example, an EHR database.

In various embodiments, the third user 515 may receive data (e.g., positional data, video data, and/or audio data) from the first user 505 and/or the second user 510. In various embodiments, positional data of the first user 505 and/or the second user 510 may be recorded by sensors attached to the body and sent via the network to the third user 515. In various embodiments, the VRTS 500 may compare the positional data received from each user to the predetermined treatment protocol, rehabilitation protocol, and/or assessment protocol being displayed to each user to determine a compliance metric. In various embodiments, one or more users may be shown the same protocol. In various embodiments, one or more users may be shown a different protocol.

In various embodiments, the protocol is received from a healthcare record server. In various embodiments, the healthcare record server has a database for storing electronic health records. In various embodiments, an electronic health record of the user may be accessed to retrieve one or more parameters related to the protocol.

In various embodiments, compliance with the predetermined rehabilitation protocol may be determined at the remote server. In various embodiments, the compliance metric may be determined as a measurement of how accurately and/or completely a user is performing a prescribed set of motions for the predetermined protocol. In various embodiments, the positional data of the user may be compared to positional data representative of the correct motions in the protocol. In various embodiments, the compliance metric may include a range of acceptable values. In various embodiments, the compliance metric may include a biometric measurement.

In various embodiments, the biometric measurement is selected from: heart rate, blood pressure, breathing rate, electrical activity of the muscles, electrical activity of the brain, pupil dilation, and perspiration.

In various embodiments, whether the biometric measurement is above a threshold is determined. When the biometric measurement is above the threshold, an additional adjustment to the training protocol is determined. The additional adjustment is applied to the training protocol until the biometric measurement is below the threshold. In various embodiments, the threshold is a target heart rate. In various embodiments, whether the biometric measurement is below a bottom threshold is determined. In various embodiments, an additional adjustment to the training protocol is determined when the biometric measurement is below the bottom threshold. The additional adjustment is applied to the training protocol until the biometric measurement is above the bottom threshold. In various embodiments, motion data and/or biometric measurements are logged in the electronic health record.

In various embodiments, when the compliance metric is below a predetermined threshold (e.g., the lower end of a range), the VRTS 500 may provide an indication to the third user 515 that the user is not complying with the protocol. In various embodiments, the third user 515 may apply an adjustment to the protocol for one or more users using the VRTS. In various embodiments, the adjustment may include providing an entirely different protocol and/or adjusting the difficulty of the protocol, e.g., to make the protocol easier. In various embodiments, adjusting the difficulty of the protocol may include adjusting the number of repetitions, adjusting the required range of motion, and/or changing the specific body part required to perform a motion to allow the body part to rest. In various embodiments, when the compliance metric is above a predetermined threshold (e.g., the higher end of a range), the VRTS 500 may provide an indication to the third user 515 that the protocol may be too easy for the user. In various embodiments, the adjustment may include providing an entirely different protocol and/or adjusting the difficulty of the protocol, e.g., to make the protocol more difficult. In various embodiments, adjusting the difficulty of the protocol may include adjusting the number of repetitions, adjusting the required range of motion, and/or changing the specific body part required to perform a motion. In various embodiments, the adjustment is logged in an electronic health record.

In various embodiments, the VRTS 500 may automatically detect compliance with a predetermined protocol for each user and adjust each user's protocol as needed to provide tailored user-specific protocols for treatment, rehabilitation, and/or training.

Figure 5B:
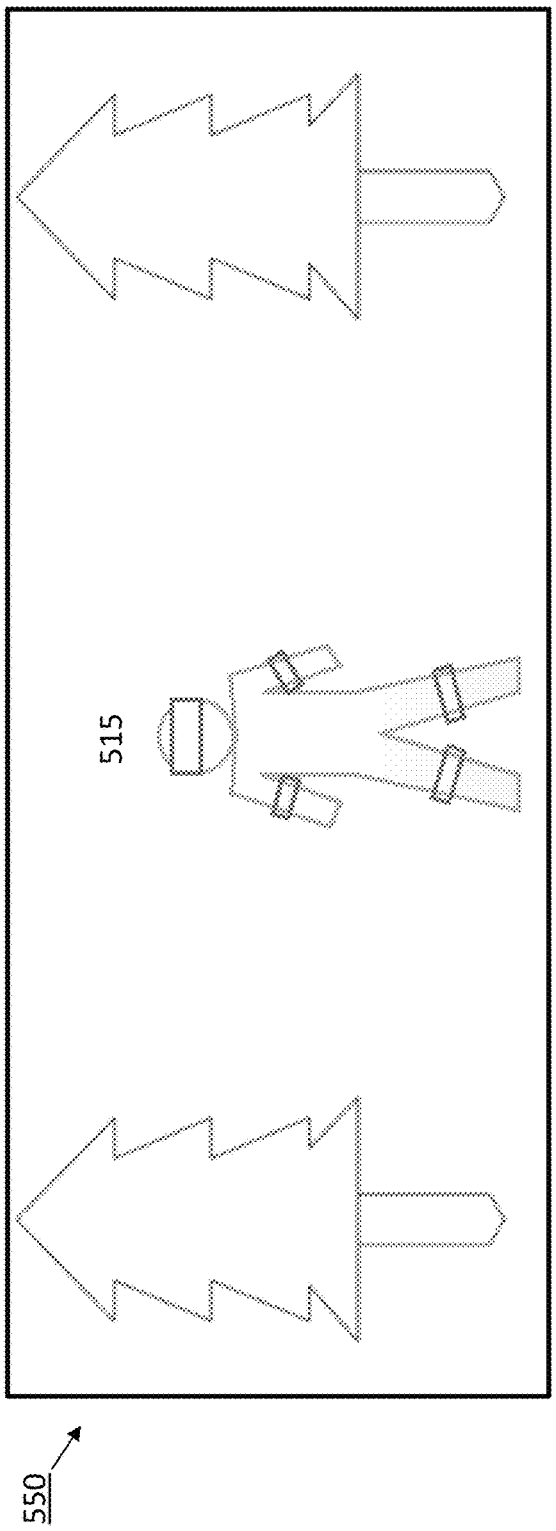
FIG. 5B is a simplified illustration of a view of two users in a virtual environment of a multi-layer real-time Virtual Reality Telecommunication system (VRTS), in accordance with an embodiment of the present disclosure.
Figure 5B:
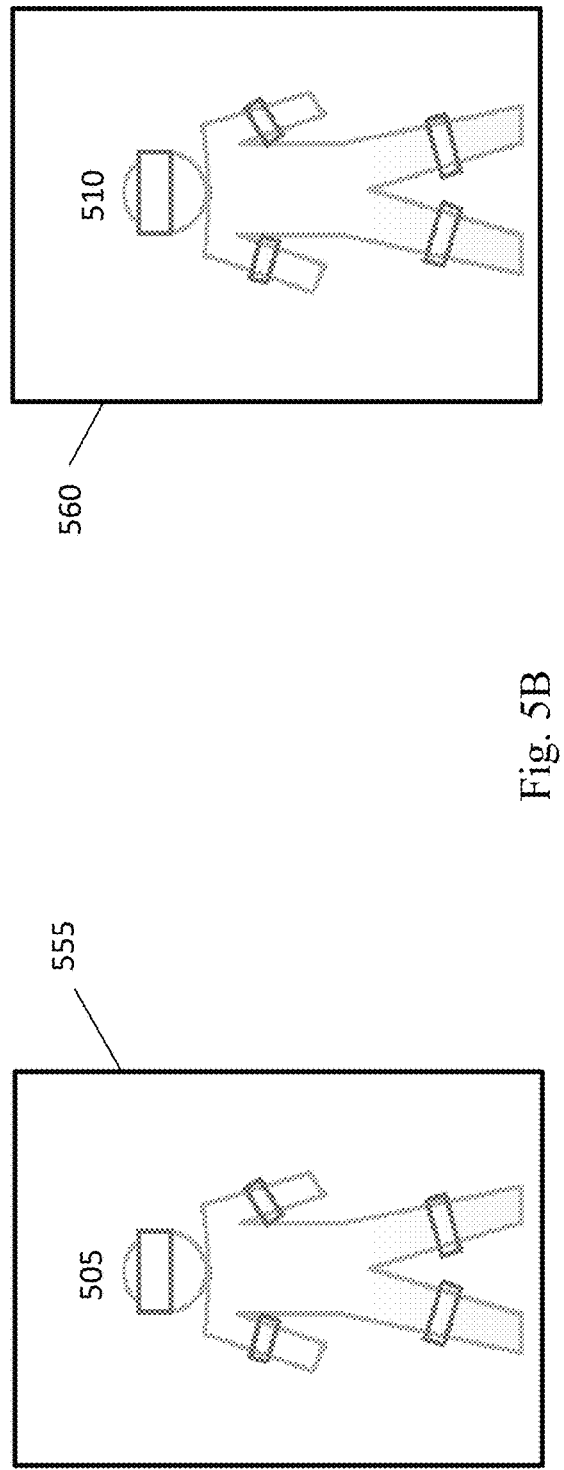

FIG. 5B is a simplified illustration of a view of two users in a virtual environment 550 of a multi-layer real-time Virtual Reality Telecommunication system (VRTS), in accordance with an embodiment of the present disclosure. In FIG. 5B, first user 505 and second user 510 are both in a virtual environment viewing a real-time feed of a third user 515 (e.g., an instructor or therapist) from a camera at a location of the third user 515. The third user 515 may direct the users to perform activities and/or demonstrate the proper procedures for performing the specific activities. In various embodiments, the third user 515 may be presented to the users as a digital avatar or other digital representation as is known in the art.

In various embodiments, the first user 505, the second user 510, and the third user 515 may each be at different locations. In various embodiments, the first user 505 and the second user 510 may be able to interact within the VRTS. For example, a training protocol may include a cooperative component where both users are required to cooperate to achieve a specific goal or outcome.

In various embodiments, the same activity protocol (e.g., treatment, rehabilitation, or assessment) may be displayed to each user 505, 510 via a virtual overlay 555, 560 in the virtual environment. In various embodiments, a different activity protocol (e.g., treatment, rehabilitation, or assessment) may be displayed to each user 505, 510 via a virtual overlay 555, 560 in the virtual environment. For example, the first user 505 may have an overlay 555 displaying a shoulder rehabilitation exercise while the second user 510 may have an overlay 560 displaying a neck range-of-motion assessment.

Figure 6:
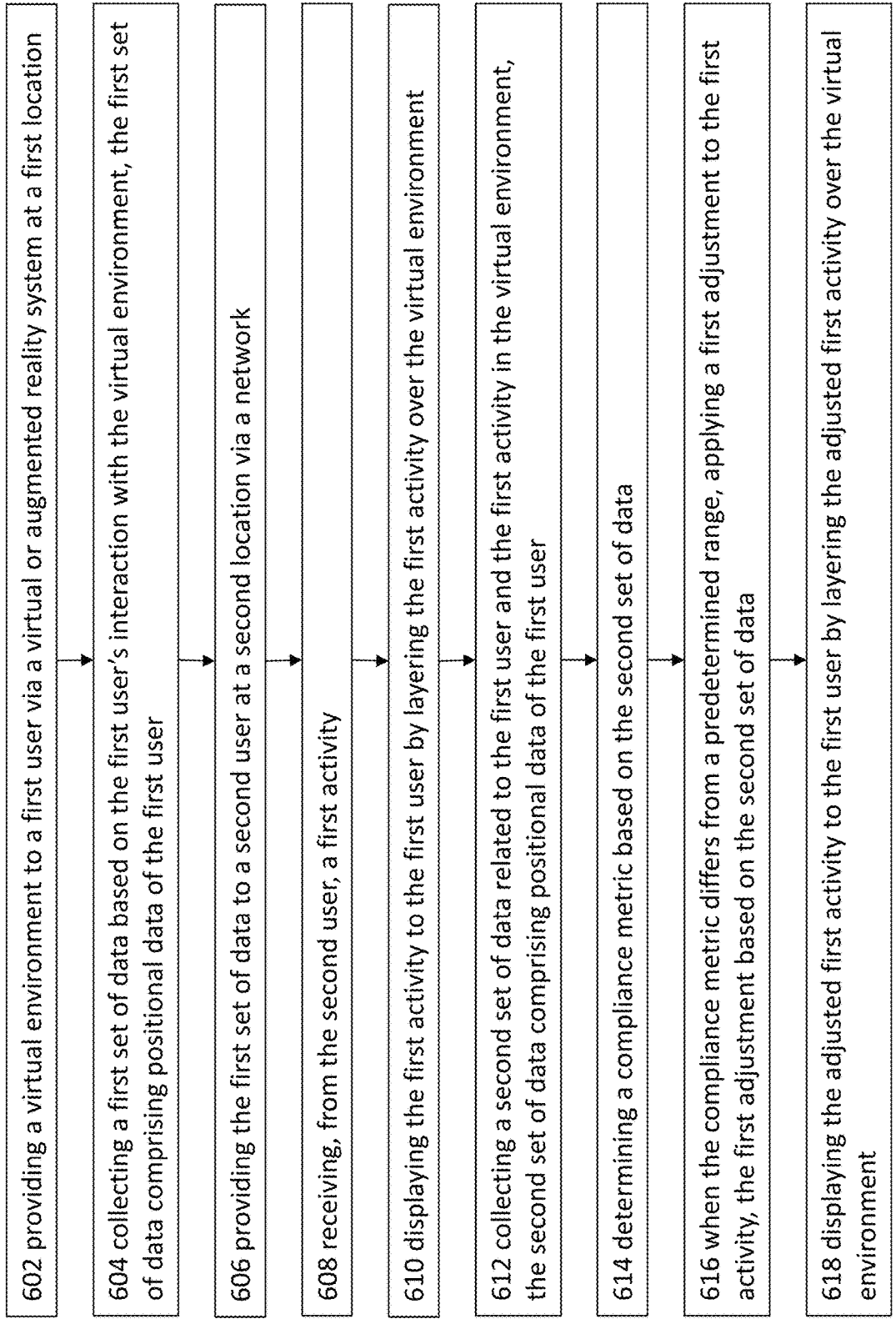
FIG. 6 is a simplified flowchart of a method of treating a user using a multi-layer real-time Virtual Reality Telecommunication System (VRTS) as shown in FIG. 2, in accordance with an embodiment of the present disclosure.

FIG. 6 is a simplified flowchart of a method 600 of treating a user using a multi-layer real-time Virtual Reality Telecommunication System (VRTS) as shown in FIGS. 2, 3, 4, 5A, and 5B, in accordance with embodiments of the present disclosure. In various embodiments, a virtual environment is provided to a first user via a virtual or augmented reality system at a first location. At 604, a first set of data is collected based on the first user's interaction with the virtual environment. The first set of data includes positional data of the first user. At 606, the first set of data is provided to a second user at a second location via a network. At 608, a first activity is received from the second user. At 610, the first activity is displayed to the first user by layering the first activity over the virtual environment. At 612, a second set of data related to the first user and the first activity in the virtual environment is collected. The second set of data includes positional data of the first user during the activity. At 614, a compliance metric is determined based on the second set of data. At 616, when the compliance metric differs from a predetermined range, a first adjustment is applied to the first activity. The first adjustment is based on the second set of data. At 618, the adjusted first activity is displayed to the first user by layering the adjusted first activity over the virtual environment.

In various embodiments, the activity is a treatment protocol. In various embodiments, the activity is an assessment protocol. In various embodiments, the activity is a rehabilitation protocol. In various embodiments, a third set of data may be collected for a third user. The third set of data may include positional data. In various embodiments, the first activity may be displayed to the third user by layering the first activity over the virtual environment. In various embodiments, a fourth set of data is collected related to the third user and the first activity in the virtual environment. The fourth set of data may include positional data of the third user during the activity. In various embodiments, a second adjustment may be applied to the first activity for the third user. The second adjustment may be based on the fourth set of data. In various embodiments, the second adjustment may be the same or different than the first adjustment.

Figure 7:
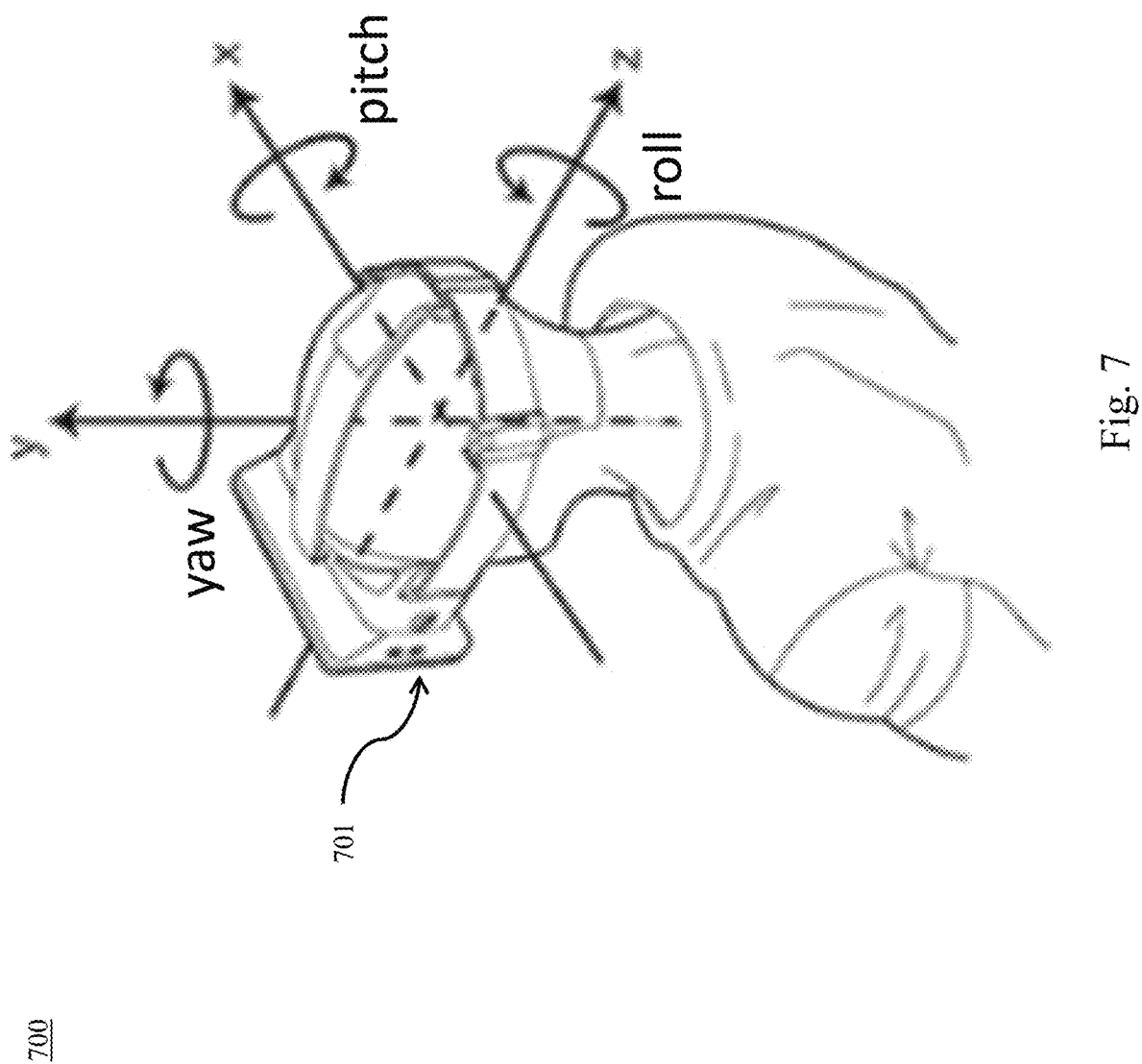
FIG. 7 illustrates an exemplary virtual reality headset according to embodiments of the present disclosure.

With reference now to FIG. 7, an exemplary virtual reality headset is illustrated according to embodiments of the present disclosure. In various embodiments, system 700 is used to collected data from motion sensors including hand sensors (not pictured), sensors included in headset 701, and additional sensors such as sensors placed on the body (e.g., torso, limbs, etc.) or a stereo camera. In some embodiments, data from these sensors is collected at a rate of up to about 150 Hz. As illustrated, data may be collected in six degrees of freedom: X—left/right; Y—up/down/height; Z—foreword/backward; P—pitch; R—roll; Y—yaw. As set out herein, this data may be used to track a user's overall motion to facilitate interaction with a virtual environment and to evaluate their performance. Pitch/Roll/Yaw may be calculated in Euler angles.

In various embodiments, off the shelf VR systems are optionally used with additional external compatible sensors to track various elements in multiple fields including, e.g., motion tracking, cognitive challenges, speech recognition, stability, facial expression recognition, and biofeedback.

Motion tracking can include, but is not limited to tracking of gait, stability, tremors, amplitude of motion, speed of motion, range of motion, and movement analysis (smoothness, rigidity, etc.).

Cognitive challenges can include, but is not limited to reaction time, success rate in cognitive challenges, task fulfillment according to different kind of guidance (verbal, written, illustrated, etc.), understanding instructions, memory challenges, social interaction, and problem solving.

Speech Recognition can include, but is not limited to fluent speech, ability to imitate, and pronunciation.

Stability can include, but is not limited to postural sway.

Bio-Feedback can include, but is not limited to, Heart rate variability (HRV), Electrothermal activity (EDA), Galvanic skin response (GSR), Electroencephalography (EEG), Electromyography (EMG), Eye tracking, Electrooculography (EOG), Patient's range of motion (ROM), Patient's velocity performance, Patient's acceleration performance, and Patient's smoothness performance.

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

Figure 8:
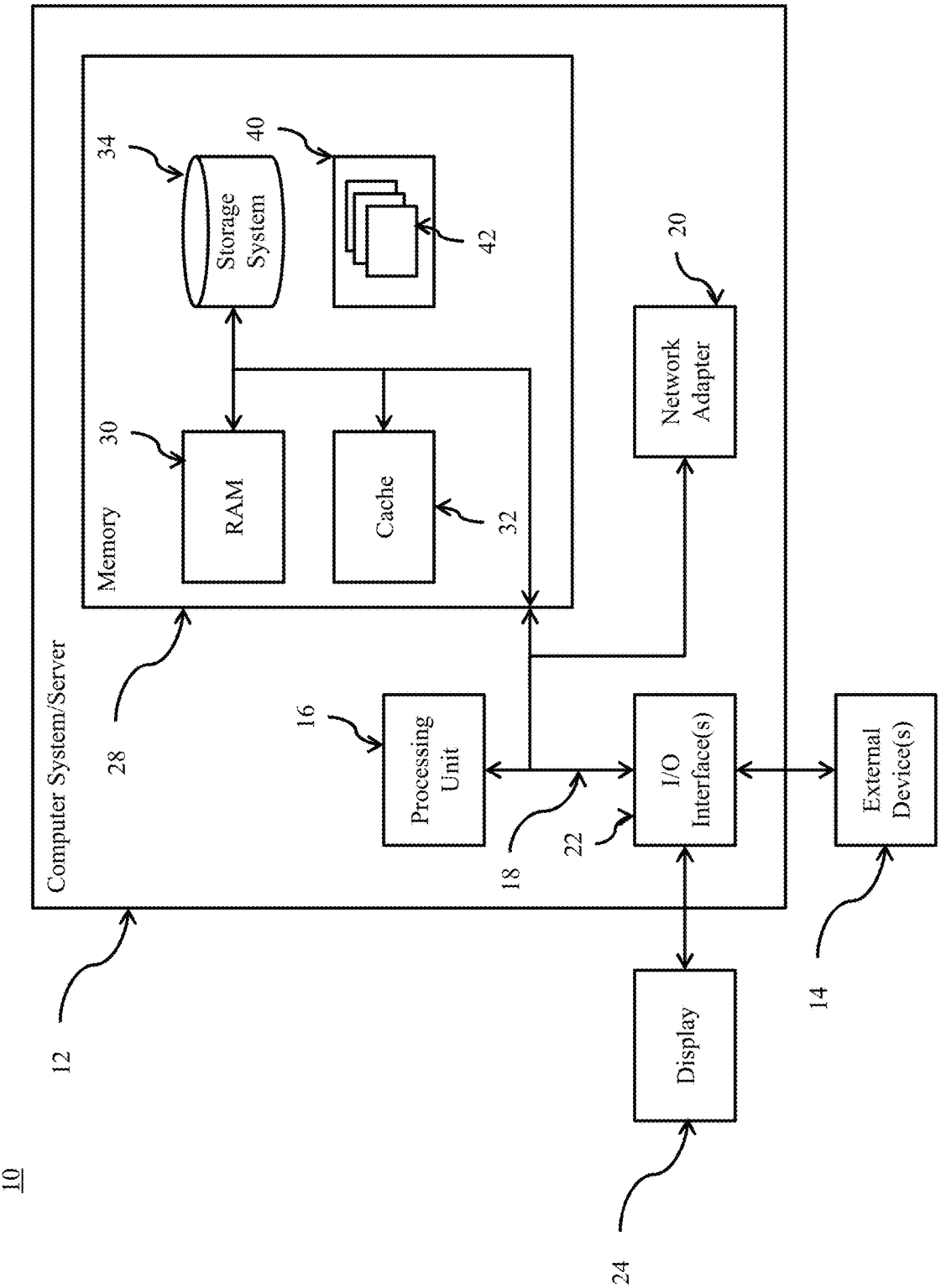
FIG. 8 depicts a computing node according to an embodiment of the present invention.

Referring now to FIG. 8, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
providing a virtual environment to a first user via a virtual or augmented reality system at a first location;
collecting a first set of data based on the first user's interaction with the virtual environment, the first set of data comprising positional data of the first user;
providing the first set of data to a second user at a second location via a network;
receiving, from the second user, a first activity;
displaying the first activity to the first user by layering the first activity over the virtual environment;
collecting a second set of data related to the first user and the first activity in the virtual environment, the second set of data comprising positional data of the first user;
determining a compliance metric based on the second set of data;
when the compliance metric differs from a predetermined range, applying a first adjustment to the first activity, the first adjustment based on the second set of data;
displaying the adjusted first activity to the first user by layering the adjusted first activity over the virtual environment;

providing the virtual environment to a third user at a third location via the virtual or augmented reality system, wherein the third user is enabled to interact with the first user;

collecting a third set of data based on the third user's interaction with the virtual environment, the third set of data comprising positional data of the third user;

displaying the first activity to the third user by layering the first activity over the virtual environment;

collecting a fourth set of data related to the third user and the first activity in the virtual environment, the fourth set of data comprising positional data of the third user; and applying a second adjustment to the first activity for the third user, the second adjustment based on the fourth set of data.

2. The method of claim 1, wherein the first activity is a treatment protocol.

3. The method of claim 1, wherein the first activity is an assessment protocol.

4. The method of claim 1, wherein the first activity is a rehabilitation protocol.

5. The method of claim 1, wherein the second adjustment is different from the first adjustment.

6. The method of claim 1, wherein the second adjustment is the same as the first adjustment.

7. A system comprising:
   a virtual or augmented reality system, comprising a virtual or augmented reality display adapted to display a virtual environment to a first user;
   one or more biometric sensors coupled to the first user;
   a computing node comprising a computer readable storage medium having program instructions embodied therewith, the program instructions executable by a processor of the computing node to cause the processor to perform a method comprising:
   providing a virtual environment to a first user via the virtual or augmented reality system at a first location;
   collecting a first set of data from the one or more biometric sensor based on the first user's interaction with the virtual environment, the first set of data comprising audio data and positional data of the first user;
   providing the first set of data to a second user at a second location via a network;
   receiving, from the second user, a first activity;
   displaying the first activity to the first user by layering the first activity over the virtual environment;
   collecting a second set of data related to the first user and the first activity in the virtual environment, the second set of data comprising audio data and positional data of the first user;
   determining a compliance metric based on the second set of data;
   when the compliance metric differs from a predetermined range, applying a first adjustment to the first activity, the first adjustment based on the second set of data;
   adjustment to the first activity, the first adjustment based on the second set of data; and displaying the adjusted first activity to the first user by layering the adjusted first activity over the virtual environment;
   providing the virtual environment to a third user at a third location via the virtual or augmented reality system, wherein the third user is enabled to interact with the first user;
   collecting a third set of data based on the third user's interaction with the virtual environment, the third set of data comprising positional data of the third user;
   displaying the first activity to the third user by layering the first activity over the virtual environment;
   collecting a fourth set of data related to the third user and the first activity in the virtual environment, the fourth set of data comprising positional data of the third user; and
   applying a second adjustment to the first activity for the third user, the second adjustment based on the fourth set of data.

8. The system of claim 7, wherein the first activity is a treatment protocol.

9. The system of claim 7, wherein the first activity is an assessment protocol.

10. The system of claim 7, wherein the first activity is a rehabilitation protocol.

11. A computer program product for providing a virtual or augmented reality platform, the computer program product comprising a computer readable storage medium having program instructions embodied therewith, the program instructions executable by a processor to cause the processor to perform a method comprising:
   providing a virtual environment to the first user via a virtual or augmented reality system at a first location;
   collecting a first set of data based on the first user's interaction with the virtual environment, the first set of data comprising positional data of the first user;
   providing the first set of data to a second user at a second location via a network;
   receiving, from the second user, a first activity;
   displaying the first activity by layering the first activity over the virtual environment;
   collecting a second set of data related to the user and the first activity in the virtual environment, the second set of data comprising positional data of the first user;
   determining a compliance metric based on the second set of data;
   when the compliance metric differs from a predetermined range, applying an adjustment of the first activity, the first adjustment based on the second set of data;
   adjustment to the first activity, the first adjustment based on the second set of data; and displaying the adjusted first activity to the first user by layering the adjusted first activity over the virtual environment;
   providing the virtual environment to a third user at a third location via the virtual or augmented reality system, wherein the third user is enabled to interact with the first user;
   collecting a third set of data based on the third user's interaction with the virtual environment, the third set of data comprising positional data of the third user;
   displaying the first activity to the third user by layering the first activity over the virtual environment;
   collecting a fourth set of data related to the third user and the first activity in the virtual environment, the fourth set of data comprising positional data of the third user; and
   applying a second adjustment to the first activity for the third user, the second adjustment based on the fourth set of data.

* * * * *